Figure 1:
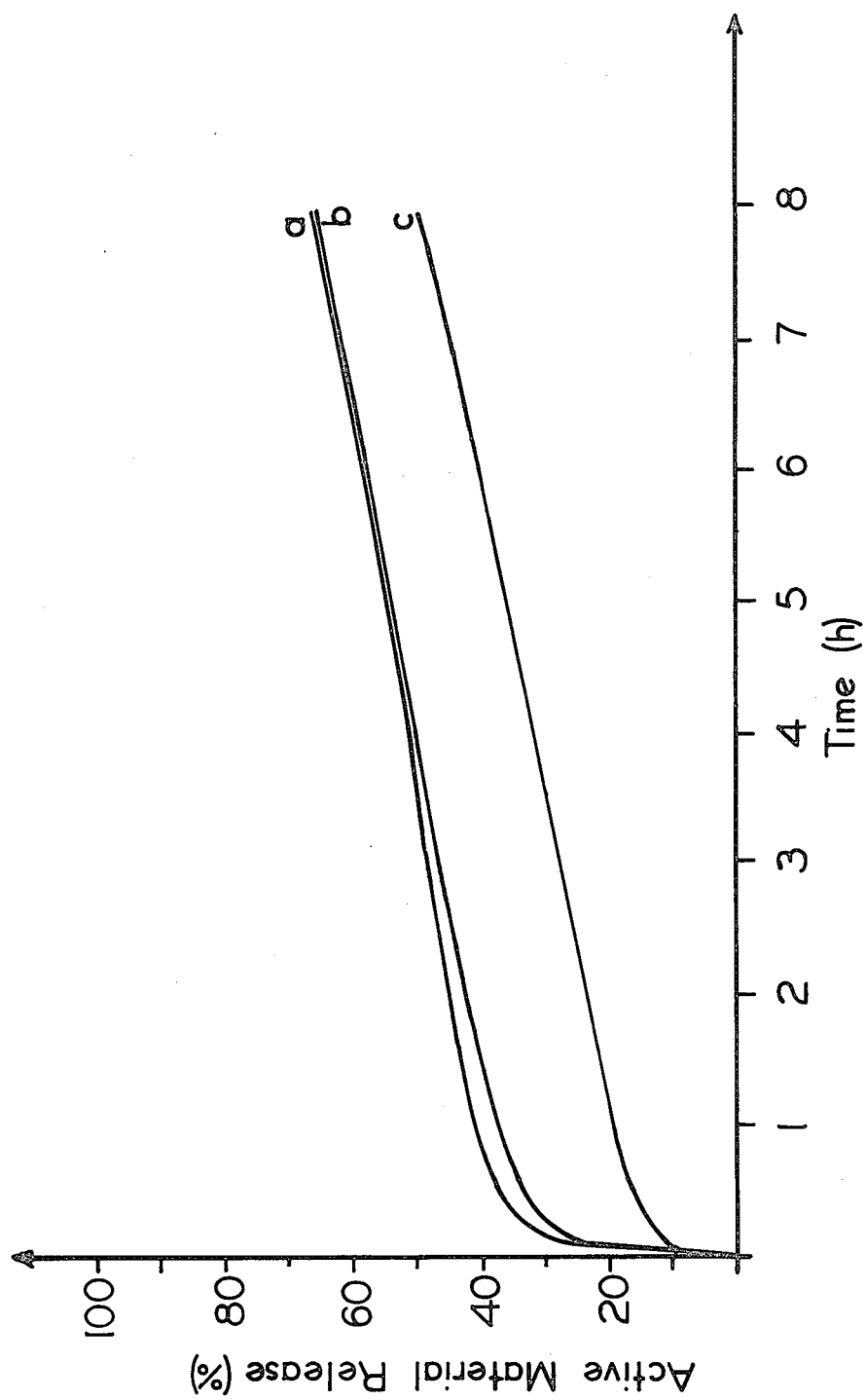

United States Patent [19]

Unger et al.

[11] 4,169,069
[45] Sep. 25, 1979

[54] SILICON DIOXIDE-CONTAINING COMPOSITIONS AND PROCESS FOR THEIR PREPARATION AND USE

[75] Inventors: Klaus Unger; Horst Kramer, both of Darmstadt; Herbert Rupprecht, Regensburg; Wolfgang Kircher, Munich, all of Fed. Rep. of Germany

[73] Assignee: Merck Patent Gesellschaft mit beschrankter Haftung, Darmstadt, Fed. Rep. of Germany

[21] Appl. No.: 834,024

[22] Filed: Sep. 16, 1977

[30] Foreign Application Priority Data

Sep. 18, 1976 [DE] Fed. Rep. of Germany ....... 2642032

[51] Int. Cl.$^2$ ..................... B01J 13/02; A01N 17/00; A61K 9/26
[52] U.S. Cl. .......................................... 252/316; 8/79; 71/64 F; 252/522; 424/19; 424/22; 424/32; 424/247; 424/260; 424/330

[58] Field of Search .................... 252/316; 424/19, 22, 424/32

[56] References Cited

U.S. PATENT DOCUMENTS

| | | | |
|---|---|---|---|
| 2,800,457 | 7/1957 | Green et al. | 252/316 |
| 3,384,680 | 5/1968 | Lussow | 252/316 X |
| 3,730,905 | 5/1973 | Koerner et al. | 252/316 |
| 3,922,392 | 11/1975 | Kohlschütter et al. | 427/215 |

*Primary Examiner*—Richard D. Lovering
*Attorney, Agent, or Firm*—Millen & White

[57] ABSTRACT

A process for the incorporation of active materials into silicon dioxide-containing carrier materials, comprises encapsulating the active material with liquid polyalkoxysiloxane polyorganoalkoxysiloxane or a mixture thereof and subsequently effecting hydrolytic polycondensation of the siloxane. The resultant enveloped active material has readily controllable release properties.

12 Claims, 11 Drawing Figures

SILICON DIOXIDE-CONTAINING COMPOSITIONS AND PROCESS FOR THEIR PREPARATION AND USE

BACKGROUND OF THE INVENTION

This invention concerns silicon dioxide-containing compositions and a process for the preparation thereof whereby active materials are incorporated therein such that the active materials are stabilized and/or their rate of liberation is controlled.

In formulating active materials, especially pharmaceutical or pest combating agents, various processes have been employed to mask flavor, reduce volatility, stabilize against oxidative and/or hydrolytic decomposition, achieve better handling during production and administration etc. Recently, measures to control the rate of liberation of active materials, i.e., to achieve a desired retarding has received much attention, e.g., for the production of depot pharmaceuticals. The most important retardation technique involves binding of the active material to carrier substances or embedding of the pharmaceuticals in suitable encapsulating or matrix substances.

When embedding into a matrix or binding onto a carrier via asorptive forces or ion exchange is employed, in addition to a large number of organic adjuvant materials (macromolecules, fats), inorganic materials such as barium sulphate, calcium sulphate, calcium phosphate, titanium dioxide and the like are also recommended. However, for the encapsulating of particles, organic substances, mostly natural, semi-synthetic or synthetic macromolecules, are used exclusively. A large range of suitable adjuvant materials is thereby available, comprising essentially hydrophilic colloids, such as gum arabic, gelatine, cellulose ethers or swellable materials, such as methacrylic acid derivatives, cellulose esters, as well as plastics, such as PVP, polyamide, polyethylene, polyacrylates, polystyrene and a series of other mixed polymers.

In spite of this multiplicity of adjuvant materials, and of a highly developed technology, conventional formulations exhibit a series of disadvantages which, in part, considerably limit their application and also lessen the reliability of achieving the desired liberation features. This is especially true for conventional depot formulations.

On the other hand, especially when organic adjuvant materials are used, liberation of the active material in the gastrointestinal tract is very difficult to control. This disadvantage is due to the fact that the liberation of the active material by diffusion from a matrix or through porous capsule walls or after dissolution of an encapsulating material, is very considerably dependent upon the conditions of the surroundings, such as e.g. pH, ion concentration, enzyme influences and the like. Due to these conditions, dissolution or swelling of the matrix or enveloping substances often occurs, whereby the ensuing nature and rate of liberation of the active material often cannot be anticipated. In many cases, the complete availability of the active materials is impaired by binding to carriers, whereby exact dosaging becomes difficult.

On the other hand, compatibility of the active material with the carriers is often unsatisfactory, especially in the pharmaceutical field. For example, the adjuvant materials can burden the digestive tract or may even be fully incompatible for certain patients, e.g., those who must avoid sugars, fats, etc. Moreover, due to expansion and/or swelling of materials, unpleasant feelings of satiation can be produced and even potential danger can exist if the polymers used still contain residual parts of toxic components, such as, e.g., catalysts, accelerators, hardeners, plasticisers, stabilizers, filling materials or unreacted monomers.

Furthermore, due to the very large number of recommended adjuvant and additional materials, an enormous number of combinations are possible. Consequently, the development of a pharmaceutical form for a new active material becomes a time-consuming and expensive proposition. In addition, the formulation process itself, e.g, microencapsulation, requires a high degree of precision with attendant complicated and expensive apparatus when reproducable results are required.

SUMMARY OF THE INVENTION

Accordingly, it is an object of this invention to provide a process of incorporating active materials into carriers which not only can be carried out with simple adjuvant materials, but which also permits the liberation behavior of the active materials in question to be directly controlled by selection of a few easily controllable parameters.

It is another object of this invention to provide such a process which employs a readily compatible, non-toxic and non-digestable carrier material which retains its essential structure independent of the surrounding medium, and thereby renders possible a complete liberation of the active material, especially a pharmaceutical, with reproducible speed.

Surprisingly, it has now been found that these objects can be achieved simply, by incorporating active materials in a novel manner into silicon dioxide-containing carrier materials.

In a process aspect, this invention relates to a process for the incorporation of active materials into a silicon dioxide-containing carrier material, which comprises encapsulating the active materials, optionally together with additional carrier materials, with liquid polyalkoxy and/or polyorganoalkoxysiloxanes and subsequently effecting hydrolytic polycondensation of the enveloping material.

Polyalkoxysiloxanes and polyorganoalkoxysiloxanes containing alkoxy groups having 1–4 carbon atoms are preferred.

In a composition aspect, this invention relates to silicon dioxide-containing active material compositions which comprise active materials which are incorporated in silicon dioxide and/or organic-modified silicon dioxide as defined herein, produced by hydrolytic polycondensation of polyalkoxy- and/or polyorganoalkoxysiloxanes, the $SiO_2$ having a selectable and reproducible pore structure.

In a method of use aspect, this invention relates to a method of administering an active ingredient with a desired liberation rate which comprises administering the active ingredient incorporated in silicon dioxide and/or organic-modified silicon dioxide as defined herein, produced by hydrolytic polycondensation of polyalkoxy- and/or polyorganoalkoxysiloxanes, the $SiO_2$ having a selectable and reproducible pore structure.

DETAILED DISCUSSION

The process of this invention and the compositions produced thereby exhibit a series of advantages. For the process, a very good reproducibility of results is achieved without use of expensive apparatus and/or complicated techniques. The carrier and enveloping material possess a precisely definable pore structure which can be reproducibly selected within a wide range. Moreover, they suffer no changes due to swelling in the physiological medium of the gastrointestinal tract. Excellent compatibility with the active ingredient is provided, since all of the starting materials and the final encapsulating material are fully compatible. In particular, however, the desired liberation behavior can be directly controlled by selection of a few easily controllable parameters, such as, the average particle diameter of the active material to be enveloped, the average particle diameter of the particles obtained after encapsulating, the layer thickness and average pore diameter of the polysilicic acid gel envelope surrounding the active material and also the nature of any organo groups introduced into the additional carrier and/or enveloping material.

It is known that by hydrolytic polycondensation of polyalkoxy- or polyorganoalkoxysiloxanes, polysilicic acid gels with defined and directly controllable hollow space structures can be produced. See, for example, German Patent Specification No. 2,155,281 and published German Patent Application No. 2,357,184. A process is also known by which a non-porous material can be coated with a porous silicon dioxide. (See U.S. Pat. No. 3,922,392 and references incorporated therein.) However, these processes are used exclusively to produce sorption materials for chromatography, so that no suggestion can be deduced from them that it could be advantageous to incorporate active materials into silicon dioxide-containing carrier materials. In particular, the prior art has failed to recognize that by use of the process according to this invention, the liberation behavior of active materials can be controlled.

Surprisingly, however, using the process of this invention, quite varied types of liberation phenomena can be achieved. Thus, very rapid liberation of the active material to the surrounding medium can be effected. On the other hand, liberation of the active material can be, ab initio, delayed and made to remain constant over a period of time which can be controlled as desired. Alternatively, a definite proportion of the active material can be given off very rapidly as an initial dose while the remainder is continuously liberated over a comparatively long period of time, whereby not only the proportion of the initial dose but also the period of the continuous liberation can be selected.

All these advantages can be achieved simply and without impairment of the active materials by appropriate hydrolytic polycondensation of the enveloping material applied in liquid form. Hitherto, such an incorporation or micro-encapsulation of active materials, precisely adapted to the particular liberation requirements, was not possible.

The process of this invention can be modified in various ways, depending upon the desired liberation behavior of the active material.

According to one process variant, the solid active material is dispersed in liquid polyalkoxy or polyorganoalkoxysiloxane. The dispersion is then subjected to a hydrolytic polycondensation. The resultant solid polysilicic acid gel, possibly organo modified, contains the active material. After it is dehydrated and dried, as a rule it is also ground and sieved.

In an alternate aspect, the active material is dissolved, suspended, emulsified or otherwise dispersed in a solution of a polyalkoxy- or polyorganoalkoxysiloxane. This mixture is subsequently internally or externally catalysed to effect a hydrolytic polycondensation. After dehydration and drying, as above, the product particles are deaggregated, such as by grinding to render them suitable for use.

In still another aspect of the process of this invention, the active material is suspended in liquid polyalkoxy- or polyorganoalkoxysiloxane. Subsequently, this suspension is dispersed, with stirring, in water containing a polycondensation catalyst. After a short time, the droplets which thereby form solidify into solid, spheroidal particles of enveloped active materials. Thereafter, they are optionally washed and then dried. Grinding is not generally required.

In a further process aspect, the active material, together with a carrier material, can be encapsulated with a liquid film of polyalkoxy- or polyorganoalkoxysiloxane which, by subsequent hydrolytic polycondensation, condenses to a porous layer of polysilicic acid gel. As for the preceeding aspect, the only post-treatment is a drying process since the particle size is essentially predetermined by the carrier material.

The starting materials for the process of this invention, are polyalkoxysiloxanes and/or polyorganoalkoxysiloxanes. There are known materials whose production is described, for example, in German Patent Specification No. 2,155,281 and published German Patent Application No. 2,357,184 (U.S. Pat. No. 4,017,528), the disclosures of which are hereby incorporated by reference. Such starting materials wherein alkoxy is ethoxy are particularly preferred.

According to these conventional processes, a tetraalkoxy- or organoalkoxysilane or a mixture thereof is conveniently dissolved in a water-miscible solvent, e.g., ethanol, and mixed, with stirring at room temperature, with an appropriate amount of water. proportions of ingredients and reaction conditions are selected in accordance with the cited references to obtain the desired molecular weights, viscosity, etc. of the polyalkoxysiloxanes and/or polyorganoalkoxysiloxanes produced. The latter serves as a starting material for the process of this invention. It is in partially polycondensed form as described fully in the foregoing references. The final complete condensation occurs during the process of this invention in forming the coating on the active material.

To the silane are then added materials which provide hydrogen ions to cause hydrolysis. Carrying out this hydrolysis with aqueous hydrochloric acid is especially practical. The resultant homogeneous solution is stirred, while dry nitrogen is bubbled in, until a temperature increase can no longer be measured indicating the termination of the partial hydrolytic polycondensation, the extent of which is controlled, for example, by control of the amount of water added. The extent of condensation also controls the molecular weight and viscosity of the product obtained. Thus, the degree of completion of the polycondensation is determined by the desired values for these parameters.

Most of the solvent is distilled off from the reaction mixture. The residue obtained, which mainly contains the polyalkoxy- or polyorganoalkoxysiloxane, is advantageously tempered at an elevated temperature, preferably in the range of from 120° to 140° C., for at least 24 hours. Subsequently, the tempered reaction product is treated, again at an elevated temperature (e.g. 150° to 170° C.), under reduced pressure (10⁻¹ to 10⁻³ mm Hg) in order to remove traces of solvents, water and unreacted products. All these procedures take place under a nitrogen atmosphere. A storable polyalkoxy- or polyorganoalkoxysiloxane is obtained. Its Si atoms are partially cross-linked via Si-O-Si bridges. They also still possess alkoxy groups for further condensation, and possibly organo groups. The degree of cross-linking and thus also the viscosity and the molecular weight of the product depend upon the amount of water used and thus can be varied over a wide range.

For the production of polyorganoalkoxysiloxanes, a very wide variety of organoalkoxysilanes can be used. The organo radical can essentially be chosen as desired. Basically, it need only possess stability to hydrolysis so that, during the production of the modified silicon dioxides, no undesirable change of the organic group takes place. Since the hydrolysis conditions to be employed are, however, very mild, the choice of a suitable organic radical is scarcely limited thereby.

In general, suitable organoalkoxysilanes have the formula $$R_n\text{-Si}(OR^1)_{4-n}$$

wherein R is alkyl, aryl or aralkyl, $R^1$ is alkyl of 1–4 carbon atoms and n is 1, 2 or 3, preferably 1. R may be substituted as discussed below.

Especially preferred are organotriethoxysilanes, which possess especially good spatial cross-linking capability. When R is a relatively large and bulky organic radical, n is preferably 1.

R preferably possesses at most 20 carbon atoms. Suitable alkyl radicals, have straight or branched chains. The former are preferred from the point of view of the use of the end products since the diffusion properties of a gel modified with straight chain alkyl radicals are in many cases better than those of a gel modified with bulkier branched chain alkyl radicals. Because of the ready availability of the starting materials, preferred aryl groups are phenyl and naphthyl, as well as substituted phenyl and naphthyl radicals. Preferred aralkyl radicals include benzyl and substituted benzyl radicals, as well as the corresponding naphthylmethyl radicals.

Depending upon the properties desired in the end product, all R radicals can be variously substituted not only by functional but also by inert groups. Since these substituents do not impair the process of this invention, the selection of particular substituents is not critical and detailed listing is not given. In this regard, the process of this invention is highly immune to adverse effect from the presence of any substituent. Many suitable substituents are listed in the foregoing references.

Depending upon the nature of the radical R in the starting material, there are obtained hydrophobic or hydrophilic organo-silicon dioxides. For example, with benzyl or phenyl triethoxysilane, a strong hydrophobic effect is achieved. On the other hand, hydrophilic organo-silicon dioxides are produced by the use of appropriately substituted organo-trialkoxysilanes or by appropriate substitution on the organo-silicon dioxides obtained. As a rule, according to known general principles, the more polar the substituents in the radical R are the more hydrophilic is the resulting organo-silicon dioxide and vice versa.

By appropriate selection of the amount of the modifying organo component, the specific pore volume of the finally produced silicon dioxide can be controlled. With increasing content of organo component, the specific pore volume increases strongly. Furthermore, the relative increase of the specific pore volume is influenced by the size of the radical R of the organotrialkoxysilane, i.e., the specific pore volume increases with increasing size of the radical R. (See foregoing references.)

The specific pore volume can also be selected by choice of a suitable average molecular weight or viscosity of the polyalkoxysiloxane employed. Polyalkoxysiloxanes with low viscosity are, in comparison with those with high viscosity, relatively slightly cross-linked. For a given content of organo components, the specific pore volume of an organo-silicon dioxide prepared with a low viscosity polyalkoxysiloxane is higher than that of the corresponding product obtained using highly viscous polyalkoxysiloxanes. Achievement of a specific pore volume may be accomplished by conventional procedures.

For use in the process of the invention, those polyalkoxy- or polyorganoalkoxysiloxanes are especially preferred which possess an average molecular weight of about 600 to about 3000 g./mol, corresponding to a kinematic viscosity of about 5 to about 20,000 cSt. The molecular weight can be determined by conventional methods, e.g. with a steam pressure osmometer. The thus determined values are weight average molecular weights.

The viscosity of a given polyalkoxy- or polyorganoalkoxysiloxane is directly related to the average molecular weight. Therefore, complete characterization of the polyalkoxy or polyorganoalkoxysiloxanes suitable for use in this invention, is accomplished by the foregoing specification of the nature of the alkoxy and the nature and content of optional organo groups, and by specification of the appropriate average molecular weight or viscosity selection of any of which determines the others.

If the encapsulation is accomplished by suspending or dispersing the active material in the liquid polyalkoxy- or polyorganoalkoxysiloxane, active material particles having a size from about 50 to about 500 μm. are generally employed. However, when dictated by the desired end uses, much larger and/or smaller particles can also be employed. Adjustment, of course, can be made for the added diameter due to the thickness of the coating. The viscosity of the polyalkoxy- or polyorganoalkoxysiloxane is chosen so that a uniform suspension is obtained. Therefore, the viscosity should preferably be greater than about 600 cSt.

If the active material is enveloped by treatment with a solution of the polyalkoxy- or polyorganoalkoxysiloxane in an organic solvent, the viscosity of the siloxane used only plays a subordinate role. For example, the solubility of the siloxane decreases with increasing viscosity, i.e., molecular weight. Thus, the viscosity must be chosen accordingly. Suitable solvents include those which, on the one hand, are able to dissolve the polyalkoxy- or polyorganoalkoxysiloxane, on the other hand, are compatible with the active material used and which, in addition, after polycondensation has taken place, can easily be removed from the resultant product. Not only polar but also non-polar solvents can be used. Suitable solvents include alcohols, e.g., methanol, ethanol and n-propanol or isopropanol; ketones, e.g., acetone or methyl ethyl ketone; hydrocarbons, e.g., cyclohexane, n-pentane, benzene or toluene; ethers, e.g., diethyl ether, dioxane or tetrahydrofuran; and other solvents which satisfy the mentioned criteria.

The amount of the solvent added should generally be sufficient to produce at least about 50% solutions of the polyalkoxy- or polyorganoalkoxysiloxane, preferably from 50 to 80%. If the active material is dispersed or suspended in the solution of the polyalkoxy- or polyorganoalkoxysiloxane and not dissolved the suitable particle sizes for the active material range from 50 to about 500 μm.

When the active materials are enveloped via active material/polysiloxane suspension and subsequently subjected to a polycondensation in aqueous phase, active material particles having a diameter of about 30 to about 150 μm. should be used. These particles are first suspended in the liquid polyalkoxy- or polyorganoalkoxysiloxane and subsequently this suspension is dispersed in the aqueous phase by vigorous stirring. Active material-containing polysiloxane droplets thereby result, the size of which are dependent upon the speed of stirring. Since the droplet size determines the size of the solid active material carrier which results from the subsequent polycondensation, the speed of stirring generally should be chosen by routine experimentation so that particles result with a diameter of from about 200 to about 1000 μm. If final particles of other sizes are desired, different stirring rates can be employed. Adjustments for the thickness of the coating can also be made if necessary.

In the suspension, the aqueous phase preferably contains ammonia as the polycondensation catalyst. By adjustment of the concentration of the catalyst, the pore structure of the resultant silica gel can be influenced as described in German Patent Specification No. 21 55 281. However, especially for readily water-soluble active materials catalyst concentrations should be selected to be as high as possible in order to achieve a solidification of the droplets in the shortest possible time, preferably a few minutes. This is achieved e.g. by an approximately 25% ammonia solution. As described in German Patent Specification No. 21 55 281, the aqueous phase can also contain alcohol. However, it is preferred that no alcohol be added in order to inhibit the dissolution of the active material form the carrier particles. In addition or alternatively, materials can be added to reduce the solubility of the active material in the aqueous phase, e.g., common salt.

As mentioned above, the active material together with a carrier material can be encapsulated with a thin film of a polyalkoxy- or polyorganoalkoxysiloxane. In this embodiment, for example, active material-containing carrier particles can be mixed with a solution of a polyalkoxy- or polyorganoalkoxysiloxane, whereupon, after removal of the solvent, e.g., under reduced pressure, polysiloxane remains behind as a thin film on the surface of the particles. Any of the above-mentioned solvents can be used. The solvent is preferably chosen so that the active material will not be separated from the carrier material. The liquid polyalkoxy- or polyorganoalkoxysiloxane can alternatively be directly applied to the carrier particles without solvents.

The active material can be bound to the carrier material in various ways. For example, the active material can be adsorbed on a porous carrier material, can be pressed onto the carrier, can be microencapsulated in a carrier material or can be bound to the carrier in some other conventional manner. The ratio of this amount of active ingredient to carrier is generally from 100:1 to 1:100, preferably from 10:1 to 1:10 on a weight basis.

Suitable carrier materials include conventional materials compatible with the active ingredient, e.g., pharmaceuticals, plant protectors, pesticides etc. However, spheroidal particles of porous silicon dioxide are preferred. The spheroidal, porous silicon dioxide particles are generally selected so that they liberate the active material practically without delay. Generally, for this purpose particles with a size of 50 to 500 μm. and with an average pore diameter of 20 to 400 Å can be used. Generally, the particle size of the carrier is selected to correspond to the particle size desired for the final product in view of the end use. Adjustments for the thickness of the coating to be applied can also be made if required. The incorporation of the active material into the particles is conventional. For example, the porous silica gel particles can be brought into contact with a solution of the active material, whereby an adsorption equilibrium ensues. The particles are then separated having active material adsorbed on them. They are then dried.

After the active material is enveloped with the liquid polyalkoxy- or polyorganoalkoxysiloxane, the latter is subjected to complete hydrolytic polycondensation in a known manner in the presence of water and a catalyst. (See foregoing references.) Suitable catalysts include acids and bases. Thus, for example, as for the partial polycondensation used to prepare the liquid starting materials hydrochloric acid can be used. Basic catalysts are preferred, e.g., alkali metal hydroxides. However, ammonia or ammonium hydroxide is especially preferred. Moreover, the active material itself can constitute the catalyst, especially when present in the form of a base having a $pK_b$ value of less than 6.5.

From German Patent Specification No. 21 55 281 and published German Patent Application No. 23 57 184, it is known to add the catalyst together with an alcohol/water mixture. This procedure can be used in this invention with advantageous results, especially for polycondensations on enveloped carrier particles. However, for this use, the presence of an alcohol is not absolutely essential. The hydrolytic polycondensation, surprisingly, can also be effected by making water available in the form of water vapor. Thus, the reaction mixture can be exposed to a current of air previously passed through water. If the active material itself does not serve as catalyst, then the catalyst, e.g., ammonia gas, can also be supplied along with the water vapor-saturated air.

During this complete hydrolytic polycondensation, the Si-O-alkyl groups, still present after the first condensation in the preparation of the starting materials, are hydrolysed to Si-OH groups and the corresponding alkanol. Adjacent Si-OH groups can then further cross-link, splitting off water and forming Si-O-Si bridges, so that finally a solid, porous polysilicic acid gel results which no longer contains alkoxy groups. This polysilicic acid gel will be either pure $SiO_2$ or $SiO_2$ modified by organo groups if the starting material contained a polyorganoalkoxysiloxane.

By variation of the conditions used during the hydrolytic polycondensation, the pore structure of the resultant polysilicic acid gel can be selected in a known manner, e.g., by the selection of the nature and amount of the catalyst and of the amount of the optional solvent miscible with the polyalkoxy- or polyorganoalkoxysiloxane as disclosed in German Patent Specification No. 21 55 281. As a rule, the pore diameters of the polysilicic acid gels resulting from the hydrolytic polycondensation are between about 15 and about 400 Å.

Upon termination of the polycondensation, which usually is carried out at about 20° to 80° C. and can last from a few minutes up to several hours, the product is generally freed from adhering water, alcohol, optional solvent and catalyst. If further removal of such contaminants is necessary and/or advantageous, this can be easily accomplished by drying at an elevated temperature, e.g., 50° to 80° C., and reduced pressure, e.g., up to 50 mm.Hg. If even trace amounts of these materials are to be removed, it may be necessary to extend the drying process over several hours.

When the polycondensation does not involve discrete particles such as the carrier particles or the droplets dispersed in the aqueous phase, a deaggregation of the product into particles suitable for use is generally necessary. In general, this deaggregation can be performed by a simple grinding. By control of the fineness of the grinding and of an optional subsequent sieving, particles of an optimum size for the particular use can be obtained.

The optimum particle size of the products produced by the process of this invention will vary very greatly according to the field of use and is selected in accordance with conventional considerations for each field. In this respect, there is no limitation of the process of this invention. For example, if pharmaceutically active materials for oral administration are prepared the final particles prepared by this invention will generally have sizes from about 200 to about 2000 μm. However, for other fields of use, these values may be considerably larger or smaller.

The active material content of the products produced by the process of this invention can also be varied within wide limits. Generally, contents between 1 and 30 wt.% are suitable. When required, contents above or below this range can of course be employed. A content of about 2 to 20% is preferred. These contents, of course, are achieved by the corresponding selection of proper weight ratio between active material and polyalkoxy- or polyorganoalkoxysiloxane, suitably adjusted for weight loss due to polycondensation. Typical such ratios are from 1:5 to 1:200, preferably from 1:5 to 1:50.

The thickness of the enveloping layer is essentially dependent upon the amount of liquid polyalkoxy- or polyorganoalkoxysiloxane used with respect to the amount of active material or of active material plus carrier, and the particle size of the latter. In general, for the enveloping of active materials bound onto a carrier material, layer thicknesses from about 1 to about 20 μm. are preferred. If the particles to be used are obtained by grinding, then no uniform layer thickness will result since the broken surfaces, formed randomly by the grinding, will provide varying distances between active material particles and exposed surfaces. Some of the active material particles will be only partially covered by the porous encapsulating layer. This phenomenon can be utilized when an increased initial dose followed by a slow liberation of the remaining content of active material is desired. Also when the active material carriers are obtained by dispersion of an active material/polysiloxane suspension in an aqueous phase, the active material is, as a rule, so non-uniformly distributed that no uniform layer thickness results.

The liberation behavior of the active material carriers produced by the process of this invention can be controlled by variation of a series of parameters. Thus, as mentioned above, for active materials which have been incorporated by suspension in liquid polyalkoxy- or polyorganoalkoxysiloxane, and subsequent polycondensation, drying, grinding and sieving, liberation can be made to occur in such a manner that after a very rapid release of an initial dose, the remaining content is slowly given off over a comparatively long period of time. Surprisingly, for the pharmaceutical products produced by this process, at least when the content of active material is not too high, e.g., from 1 to 15%, after the release of the initial dose, the liberation of the remainder takes place practically continuously. Moreover, its release curve does not display an asymptotic approximation to the limiting value of complete release, as observed in the case of other conventional matrix systems. That is, complete usage of the active ingredient can be achieved.

For this system, the proportion of the initial dose is essentially determined by the choice of the relative particle sizes of the active material and of the active material carrier combination formed by the grinding step. Thus, for a given particle size of the active material, the finer one grinds the polysilicic acid gel the greater is the proportion of active material which is given off very rapidly as an initial dose since the surface area composed of active ingredient is thereby increased. This same effect, i.e., increase of the initial dose, can also be achieved for a given size of the active material carrier, by increasing the particle size of the active material. The nature of the subsequent continuous release, taking place after the liberation of the initial dose, can be controlled by selection of the reaction temperature of the polycondensation and by suitable choice of the polyalkoxy- or polyorganoalkoxysiloxane employed. An increase of the reaction temperature causes a simultaneous reduction of the initial dose and a more rapid continuous release. Temperature can be selected by routine parametric experimentation. Influence on the continuous release rate by the starting material siloxane is effected by suitable choice of hydrophobic and/or hydrophilic properties.

Release takes place in a different manner when the active material is incorporated by dissolution in the liquid polyalkoxy- or polyorganoalkoxysiloxane optionally in the presence of additional solvents, followed by subsequent polycondensation, drying, grinding and sieving. Since a complete enveloping is achieved in this case, liberation is thereby essentially dependent upon the porosity which, in turn, can be conventionally controlled as indicated above, e.g., by the amount of solvent or catalyst added. For active material carriers obtained by dispersion of an active material/polysiloxane suspension in an aqueous phase and subsequent polycondensation, liberation takes place in a manner analogous to that from a matrix system but a marked initial phase is observed. The behavior displayed by matrix systems is also exhibited by the liberation of active material from the active material carriers which are formed by enveloping active material together with a carrier material, followed by polycondensation.

For the latter process embodiment, liberation behavior can also be controlled by several other parameters. The thickness of the encapsulating layer (mantle) can be varied, for example by changing the ratio of the surface area of the carrier particles to the amount of polyalkoxy- or polyorganoalkoxysiloxane. As a rule, the layer thickness is varied between 1 and 20 μm. Furthermore, the pore size of the enveloping layer can be varied by the selection of the nature and amount of the catalyst used, such as is disclosed in German Patent Specification No. 21 55 281. According to this conventional technique, by selection of an hydroxyl ion concentration, which is preferably supplied by aqueous ammonia, in the range of from $1\times 10^{-3}$ to 1.5 moles per mole of Si in the polyalkoxy- or polyorganoalkoxysiloxane used, average pore diameters are obtained which lie in the range between about 30 and about 800 A°, respectively.

The liberation behavior is also strongly influenced by nature of the organo groups introduced into the enveloping layer by employment of a polyorganoalkoxysiloxane in the process. The polysilicic acid gel resulting after the hydrolytic polycondensation is modified by organo groups not only in the interior but also on its surface. In this way, the hydrophilic or hydrophobic character of the enveloping layer can be varied in any desired manner by selection of appropriate hydrophilic or hydrophobic organo groups by conventional considerations. The diffusion of the active material through the enveloping layer can thereby be influenced.

The active material carriers produced by the process of this invention can be used in numerous fields depending on the nature of the active ingredient. For example, pharmaceutical compositions with controllable active material liberation can be very advantageously produced for use in man and animals. Production of compositions for oral or rectal administration is preferred, but other active material carriers, e.g., for implantation, can also be readily produced.

Active materials having other uses can also be incorporated with the same success, e.g., pest combatting agents, plant protection agents, fertilizers, dyestuffs, aroma-generating materials and others. Generally, the process of this invention can always be used when controlled liberation of the active material is required or desirable.

The active material carriers can be used directly as produced by the process of this invention, but they also can be subsequently processed into a form suitable for the intended purpose. For example, they can be combined with additional carriers for adjuvant materials or even with additional active materials. The nature of the additional materials and the final form of the composition depend upon the conventional requirements of the field of use in question. For example, for production of pharmaceutical compositions, the active material carriers can be filled into capsules or pressed into dragees or tablets.

By this invention, a simple process is thus available by which compositions can be prepared which are not only especially advantageous due to their stability and compatibility, but also in that the liberation behavior of the incorporated active material can be controlled in a reproducible manner by appropriate selection of a few, readily variable parameters. By suitable variation of the above-described process characteristics, a skilled worker, very quickly and in a systematic manner, can find an optimal solution for the most complex problems regarding the controlled liberation of an active ingredient for a given use. He need only carry out a few parametric-type experiments, since the influence of the process characteristics on the structure of the silicon dioxide-containing carrier material is known from the literature. For example, depot and retard forms, compositions acting over extended time periods and those with variable initial release doses can be produced.

Without further elaboration, it is believed that one skilled in the art can, using the preceding description, utilize the present invention to its fullest extents. The following preferred specific embodiments are, therefore, to be construed as merely illustrative, and not limitative of the remainder of the disclosure in any way whatsoever.

The liberation behavior indicated in the drawings was measured "in vitro" with 100 ml. of a desorption liquid (either aqueous hydrochloric acid of pH 2 or Sörensen's buffer of pH 7.4) at a temperature of 37° C. and a stirring speed of 80 rotations per minute.

EXAMPLE 1

In 9 parts by weight of polyethoxysiloxane (kinematic viscosity 1000 cSt) was suspended, by stirring, one part by weight of codeine base (particle size 100 to 160 μm.; $pK_b$ value 6.1). The stirring was continued until, with commencing polycondensation, the viscosity increased strongly. To complete the polycondensation, the mixture was flushed with water vapor-saturated air. Thereafter, the product was dried under reduced pressure over phosphorus pentoxide, ground and sieved to a desired particle size.

The layer thickness of the enveloping layer was, on the average, about 50 μm. The pore diameter was, on the average, about 20 Å.

FIG. 1 shows:

(a) the liberation of the active material from active material carriers having a particle size of 315 to 800 μm. at a pH of 7.4

(b) as (a), only a pH of 2

(c) the liberation of the active material from active material carriers having a particle size of 800-2000 μm., at a pH of 7.4.

FIG. 1 shows that the liberation behavior is practically independent of the pH value but that the inital dose decreases with increasing particle size of the active material carrier.

EXAMPLE 2

The procedure of Example 1 was followed except that codeine base with a particle size of 315 to 800 μm. was incorporated.

Average layer thickness: above 50 μm.

Average pore diameter: above 100 Å.

Figure 2:
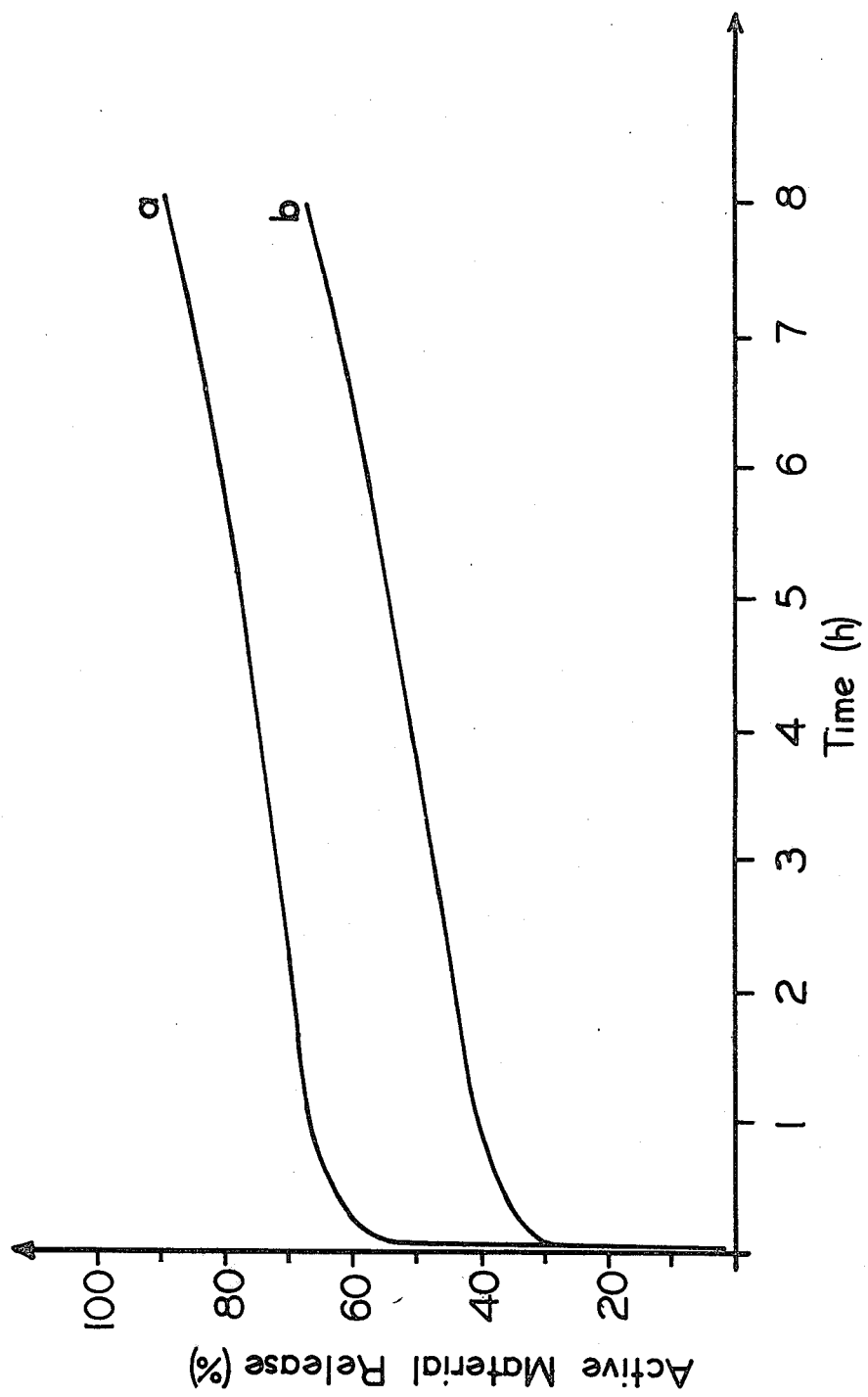

FIG. 2 shows the liberation of the active material from active material carriers with a particle size of up to 800 μm.:

(a) in the case where active material of a particle size of 315–800 μm. was employed.

(b) (From Example 1) in the case where active material of a particle size of 100–160 μm. was employed.

FIG. 2 shows that, for a given particle size of the active material carrier, the initial dose increases with increasing particle size of the active material.

EXAMPLE 3

The procedure of Example 1 was used, except that the temperature during polycondensation was increased from 20° to 80° C.

Figure 3:
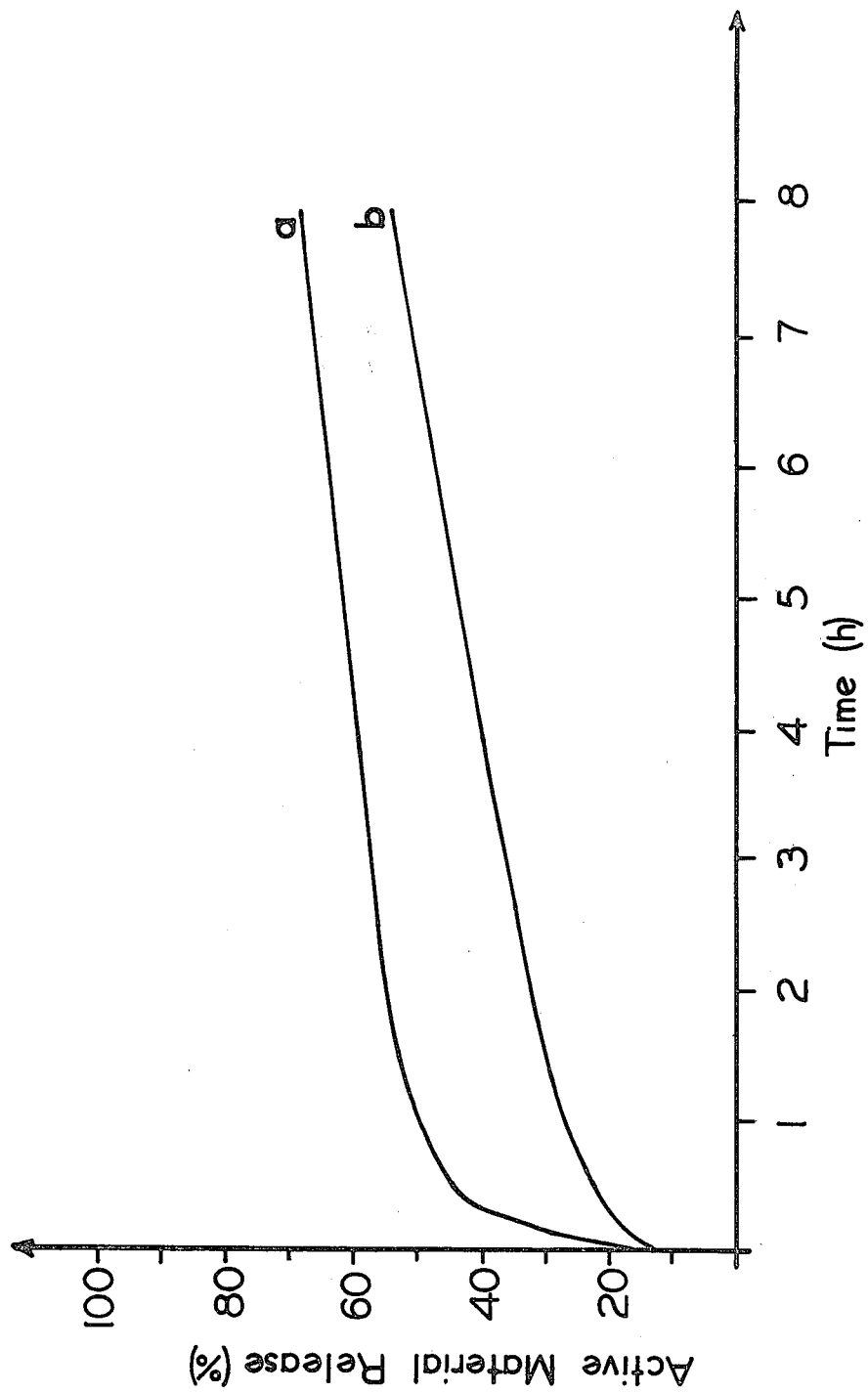

FIG. 3 shows the liberation of the active material at a pH of 7.4 from active material carriers having a particle size of 315–800 μm.:

in the case where (a), polycondensation took place at 20° C. and (b), polycondensation took place at 80° C.

Because of the larger pores, the release in (a) is faster than in (b).

Average layer thickness:
(a) about 50 μm.
(b) about 50 μm.
Average Pore diameter:
(a) about 20 Å
(b) about 15 Å

EXAMPLE 4

The procedure of Example 1 was used, except the proportion of codeine base was varied from 5 to 20 weight percent relative to the amount of polyethoxysiloxane.

Figure 4:
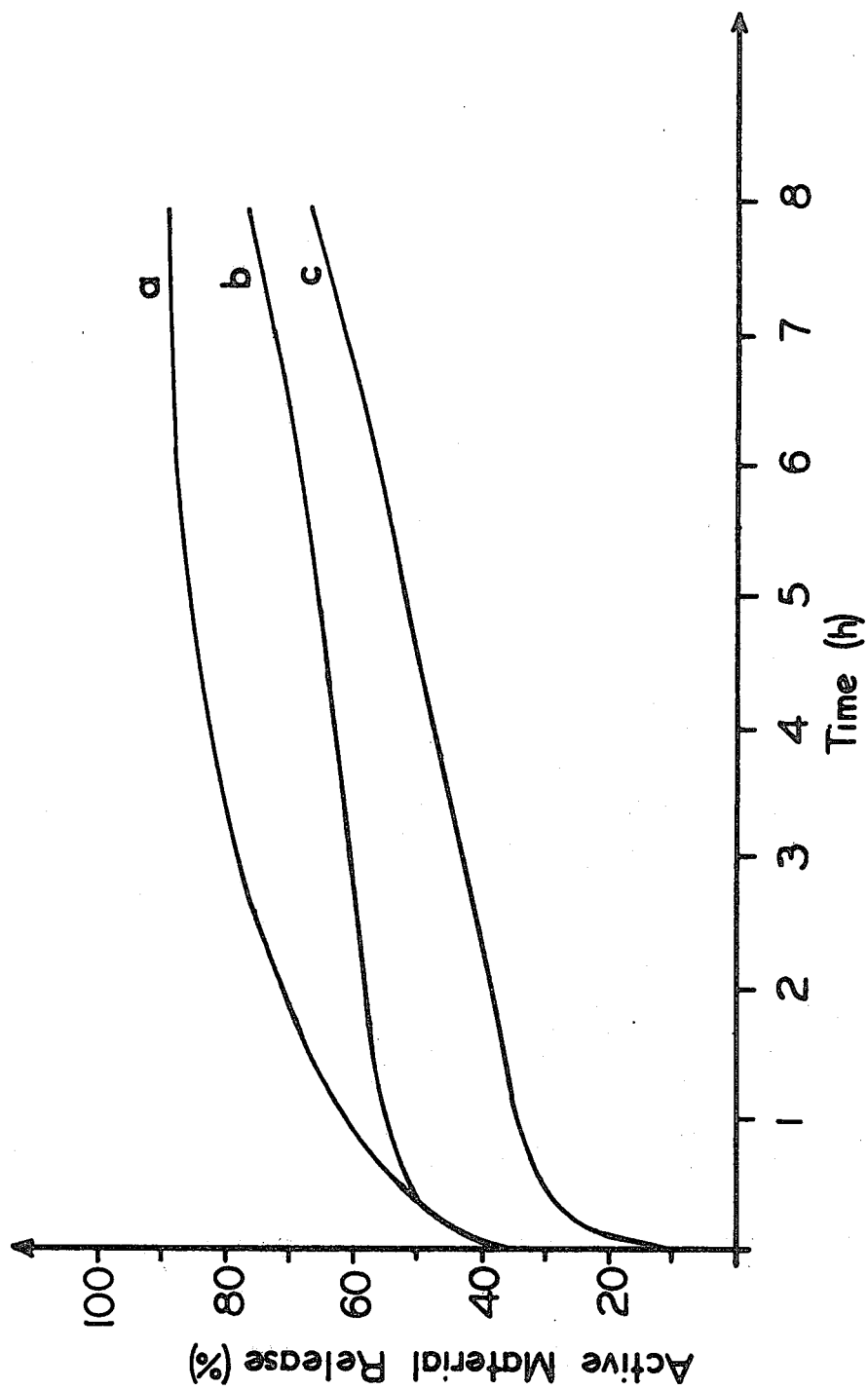

FIG. 4 shows that, with increasing active material concentration, first the initial dose is increased and that, for a higher concentration, the liberation of the active material is similar to that which is typical for matrix systems, i.e., the liberation is not uniform after the initial stage.

The size of the active material carrier was between 315 and 800 μm.; liberation medium pH: 7.4.

The active material carriers were characterized as follows:

(a) 20 wt.% codeine in the polyethoxysiloxane, corresponding to 30 wt.% in the product
average layer thickness: about 30 μm.
average pore diameter: about 20 Å
(b) 10 wt.% codeine in the polyethoxysiloxane, corresponding to 15 wt.% in the product
average layer thickness: about 50 μm.
average pore diameter: about 20 Å
(c) 5 wt.% codeine in the polyethoxysiloxane, corresponding to 7.5 wt.% in the product
average layer thickness: about 65 μm.
average pore diameter: about 20 Å

EXAMPLE 5

One part by weight polyethoxysiloxane was mixed with one part by weight of a 10% solution of codeine in acetone and further treated as in Example 1.

The product possessed an average pore diameter of about 20 Å.

Figure 5:
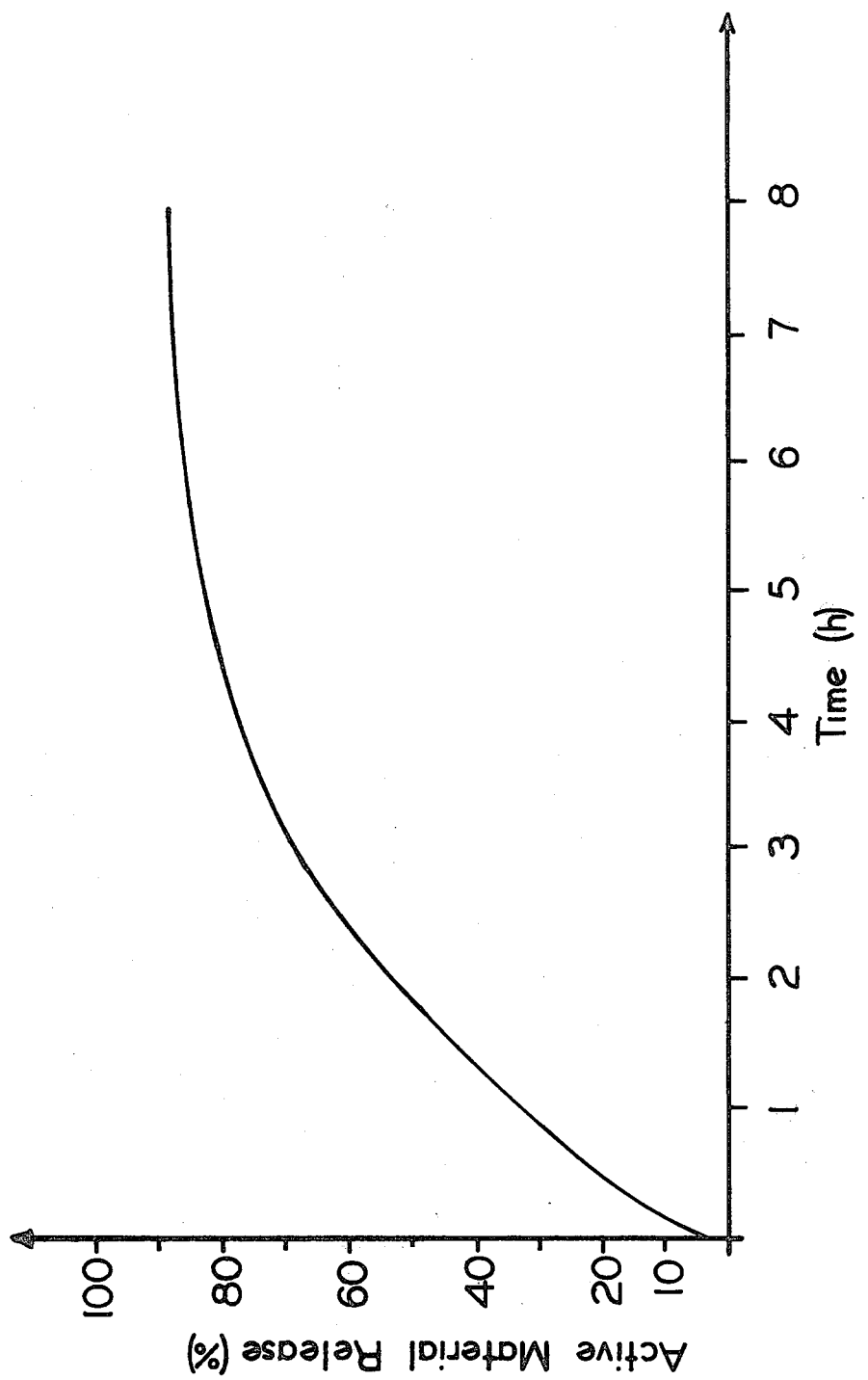

FIG. 5 shows that the liberation of the active material from this composition proceeds without an initial stage and asymptotically approaches a limiting value.

EXAMPLE 6

The procedure of Example 1 was used except that, instead of codeine, ephedrine and chlorpromazine with particle diameters of 80 to 100 μm. were used.

Figure 6:
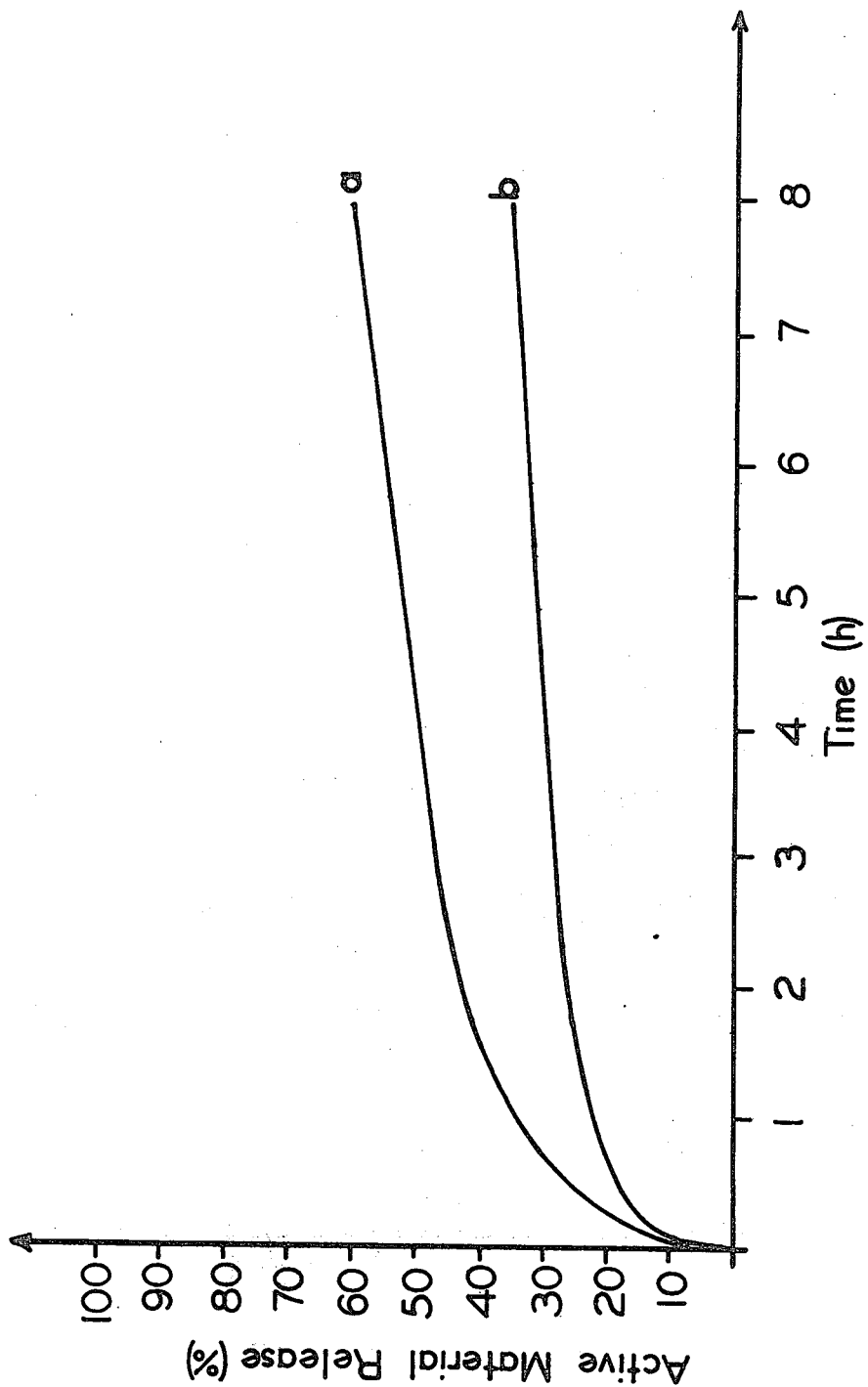

FIG. 6 shows the liberation from active material carriers with a particle size of 315–800 μm. at a pH of 7.4:

(a) contains ephedrine
average layer thickness: about 50 μm.
average pore diameter: about 20 Å
(b) contains chloropromazine
average layer thickness: about 50 μm.
average pore diameter: about 20 Å

FIG. 6 shows that the rate of liberation of ephedrine is comparable with that of codeine (FIG. 1), whereas chlorpromazine is liberated substantially more slowly.

EXAMPLE 7

A suspension of 1 part by weight of benzoic acid (particle diameter from 100 to 160 μm.) in 9 parts by weight of polyethoxysiloxane (kinematic viscosity 6000 cSt) was exposed to an air current which had been passed through an aqueous 0.5 normal ammonia solution. After hardening, the mass was freed from adhering ammonia, water and alcohol under a reduced pressure (about 50 mm.Hg) and at a temperature of 30° C. for 12 hours. It was then ground and sieved.

Potassium chloride and salicyclic acid was incorporated in the same way.

Figure 7:
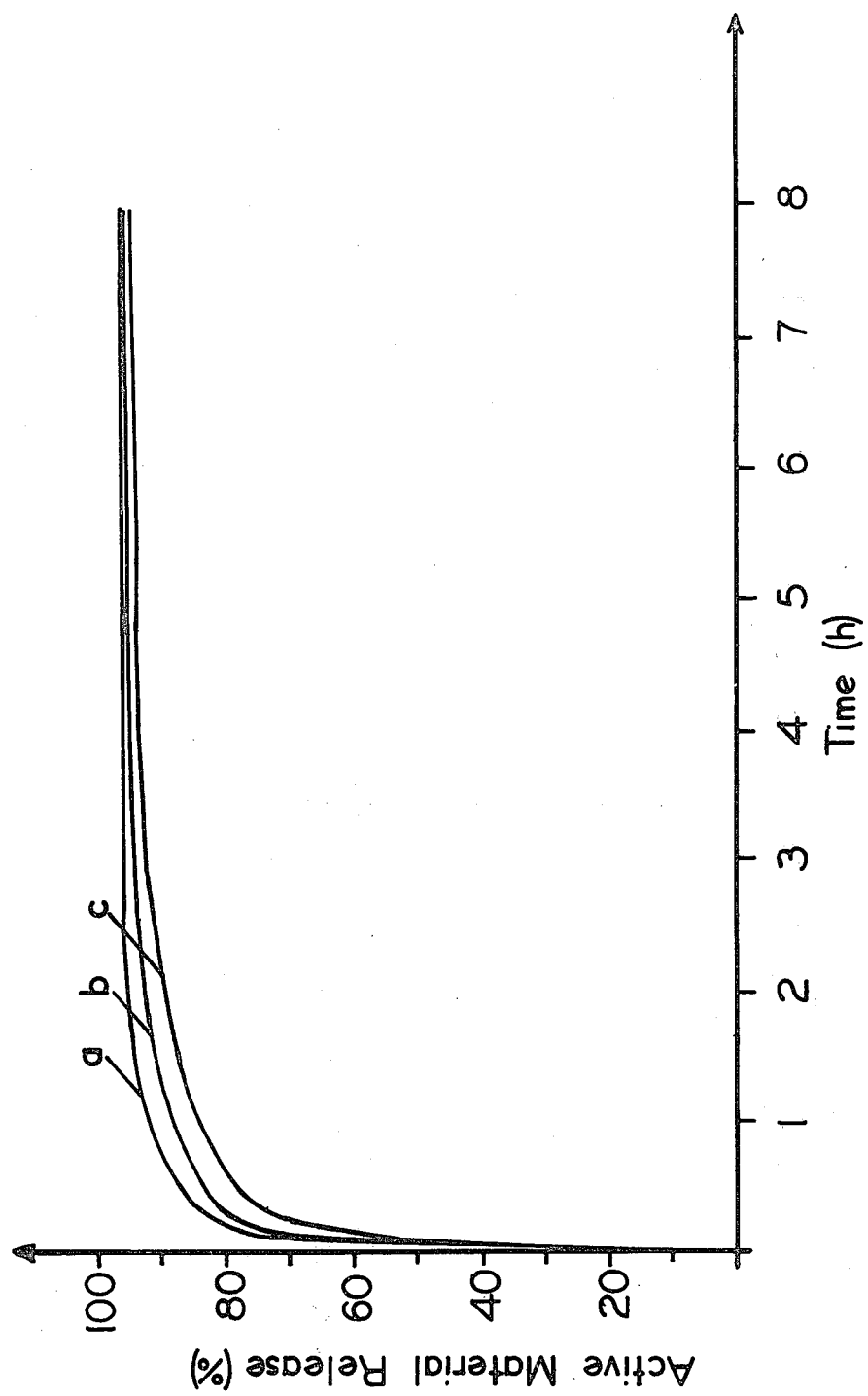

FIG. 7 shows that the liberation of the active material from these compositions produced with an external catalyst takes place very quickly.

The liberation medium was water and the particle size of the active material carrier was 315–800 μm.

(a) contains KCl
average layer thickness: about 50 μm.
average pore diameter: about 15 Å
(b) contains benzoic acid
average layer thickness: about 50 μm.
average pore diameter: about 20 Å
(c) contains salicylic acid
average layer thickness: about 50 μm.
average pore diameter: about 15 Å

EXAMPLE 8

10 g. of a microporous silicon dioxide having the following characteristics:
specific surface area $A_{BET}=2,030$ m$^2$/g.
specific pore volume $V_p=0.56$ ml./g.
average pore diameter D = 1.7 nm.
particle size dp = 100 to 125 μm.
were shaken for 3 days with 500 ml. of a 0.025 molar solution of codeine in Sörensen's phosphate buffer having a pH of 7.4. Thereby, 0.6 millimole of codeine were adsorbed per 1 g. of silica gel. The particles were separated off and dried.

0.5 g. of the so produced sorbate were mixed with a solution of 0.3 g. of polyethoxysiloxane (kinematic viscosity 600 cSt) in 15 ml. of cyclohexane. After the cyclohexane was removed at room temperature under reduced pressure, 10 ml. of a water/ethanol mixture (5:1, parts by volume) and 0.5 ml. of concentrated aqueous ammonia solution were added thereto, shaken intensively for 30 minutes, washed with 10 ml. of ether and dried for 12 hours at 60° C.

In the same way, 0.5 g. of sorbate were coated with a polyphenylethoxysiloxane, which carried a phenyl group on 30% of the Si atoms, and further treated as above.

Figure 8:
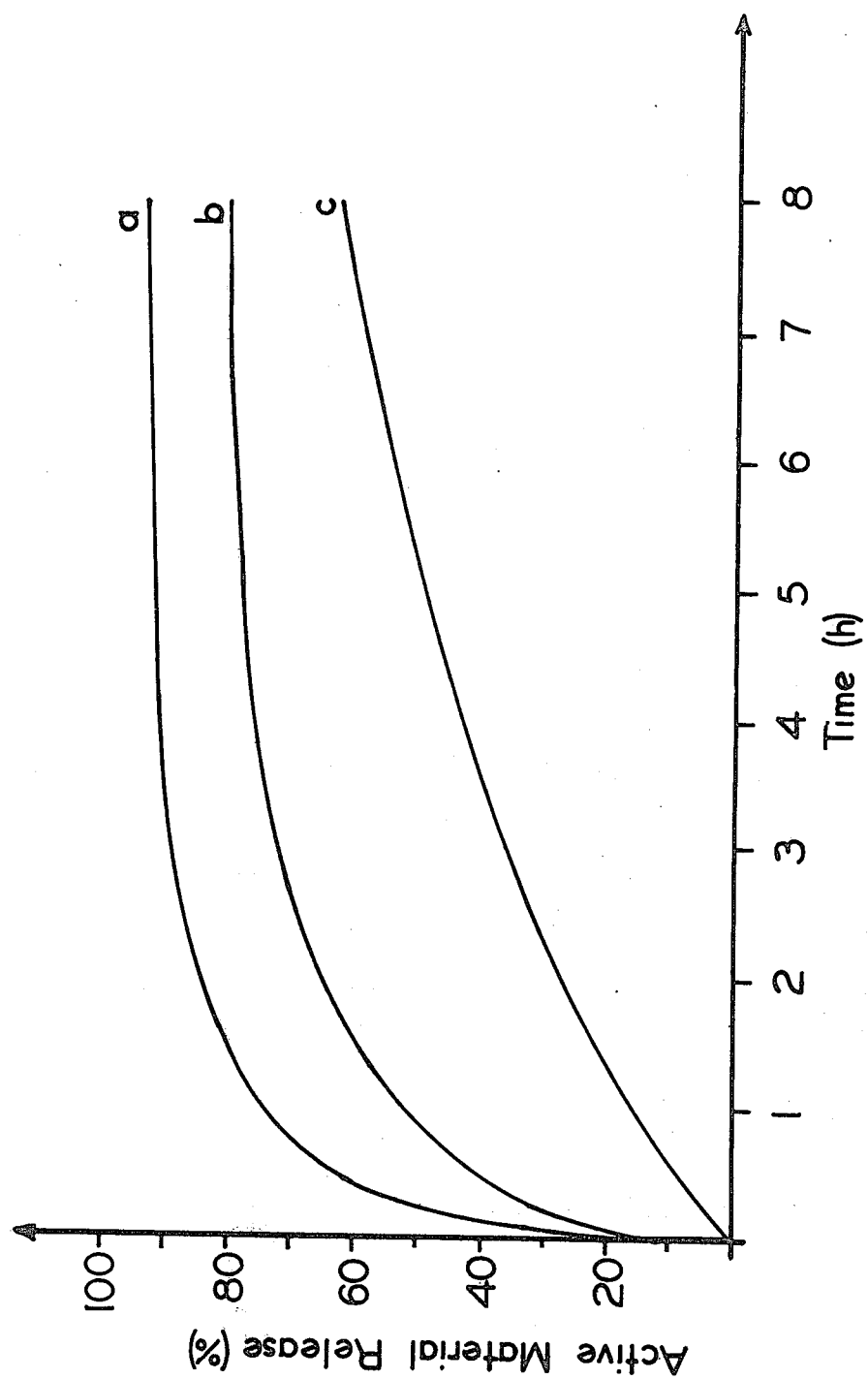

FIG. 8 shows the liberation behavior
(a) of the uncoated carrier
(b) of the carrier enveloped with polysilicic acid gel
average layer thickness: about 15 μm.
average pore diameter of the enveloping layer: about 50 Å
(c) of the carrier enveloped with polysilicic acid gel modified with phenyl groups
average layer thickness: about 15 μm.
average pore diameter of the enveloping layer: about 50 Å.

FIG. 8 shows that the liberation of the active material, which takes place very quickly from the uncoated sorbate, is delayed by enveloping with polysilicic acid gel and is delayed even more by enveloping with polysilicic acid gel modified with phenyl groups.

EXAMPLE 9

A suspension of 1 part by weight of methyl red sodium (particle diameter of 100 to 160 μm.) in 9 parts by weight of polyethoxysiloxane (kinematic viscosity of 1200 cSt) was exposed to an air current which had been passed through an aqueous 0.01 normal ammonia solution. After hardening, the mass was further treated analogously to Example 7.

Figure 9:
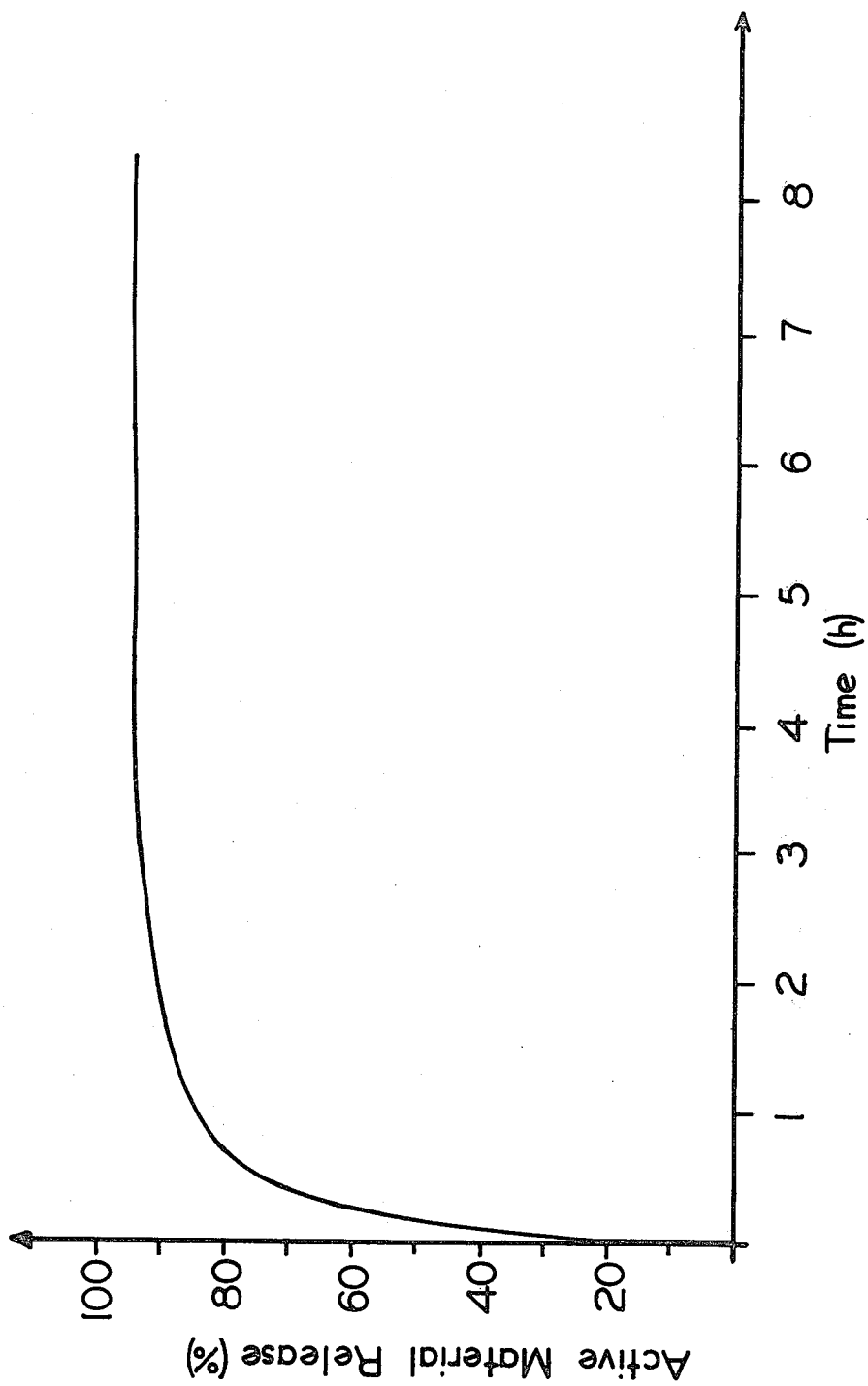

FIG. 9 shows that methyl red sodium is liberated up to 90% within 3 hours.

The liberation medium was water and the particle size of the active material carrier was 315–800 μm.

The product possessed an average layer thickness of 50 μm.; and the average pore diameter was about 20 Å.

EXAMPLE 10

7 Parts by weight of polyethoxysiloxane (kinematic viscosity of 1200 cSt) and 3 parts by weight of methylpolyethoxysiloane (prepared from 1 mole of tetraethoxysilane and 0.5 mole of methyltriethoxysilane), as well as 3.3 parts by weight of a solution of 1 part by weight of benzoic acid in 2 parts by weight of ethanol 99% were mixed.

The solution was exposed to an air current which had been passed through an aqueous 0.01 normal ammonia solution. The further treatment of the batch was analogous to that used in Example 7.

Figure 10:
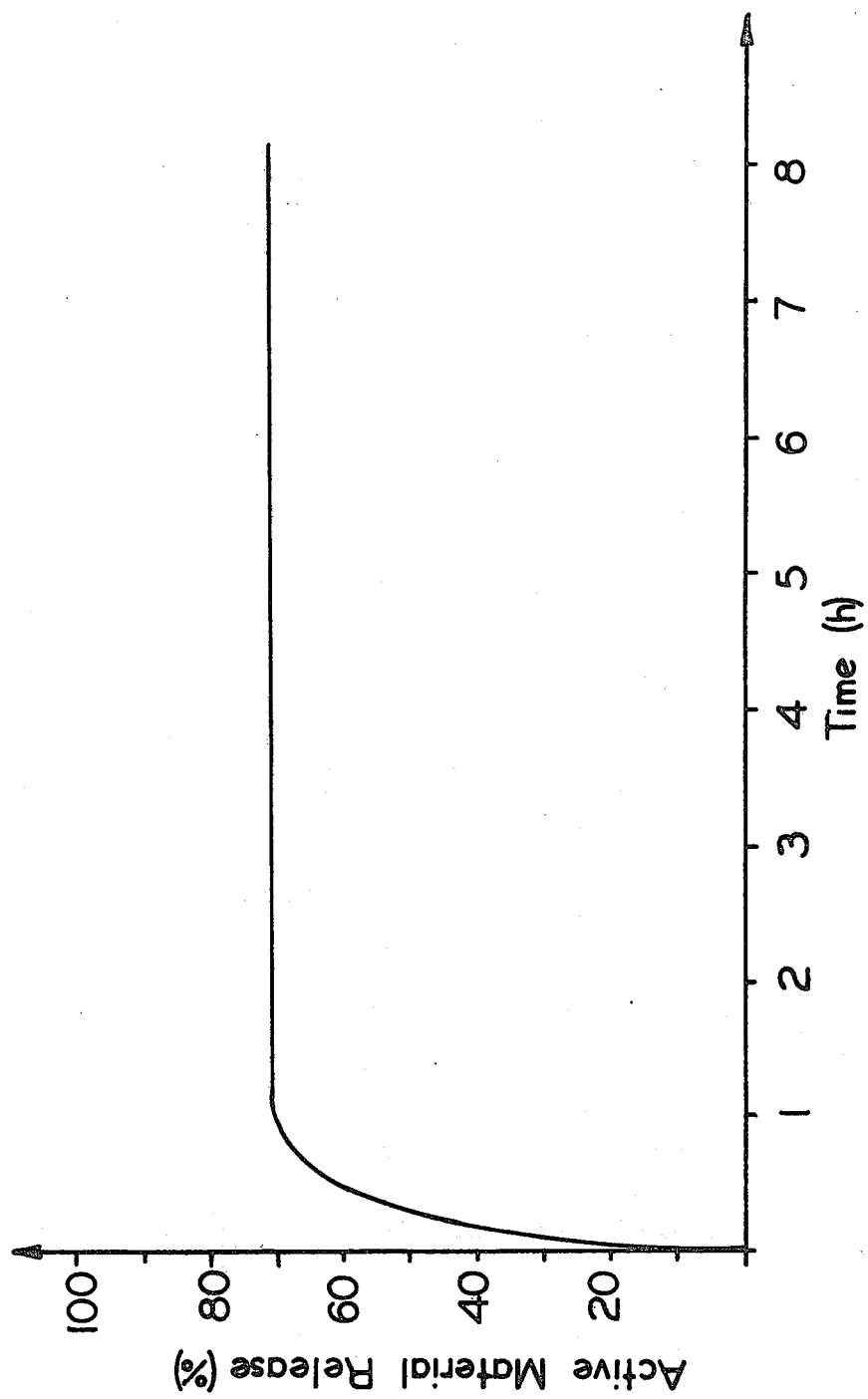

FIG. 10 shows the liberation of the benzoic acid from the active material carriers with a particle size of 315–800 μm. whereby, as compared with pure $SiO_2$ carriers (FIG. 7b), a strong delay of the liberation in the aqueous medium is shown, but also a lower availability is shown.

EXAMPLE 11

In 9 parts by weight of polyethoxysiloxane (kinematic viscosity of 1200 cSt), there was suspended one part by weight of codeine (particle size: 80–100 μm.). This suspension was subsequently dispersed in a glass beaker in 100 parts by weight of 20 wt.% sodium chloride solution containing 25% aqueous ammonia, with strong stirring (1600 rpm). The droplets formed solidified in the course of about 2 minutes. The supernatant liquid was thereafter filtered off through a frit with suction. The remaining solid was washed with 50 ml. of a 30% sodium chloride solution an then dried for 12 minutes at 50° C., 50 mm.Hg. Round spheroids were formed.

The active material carrier was characterized as follows:

particle size: 355–800 μm
average layer thickness: 50 μm.
average pore diameter: about 30 Å

Figure 11:
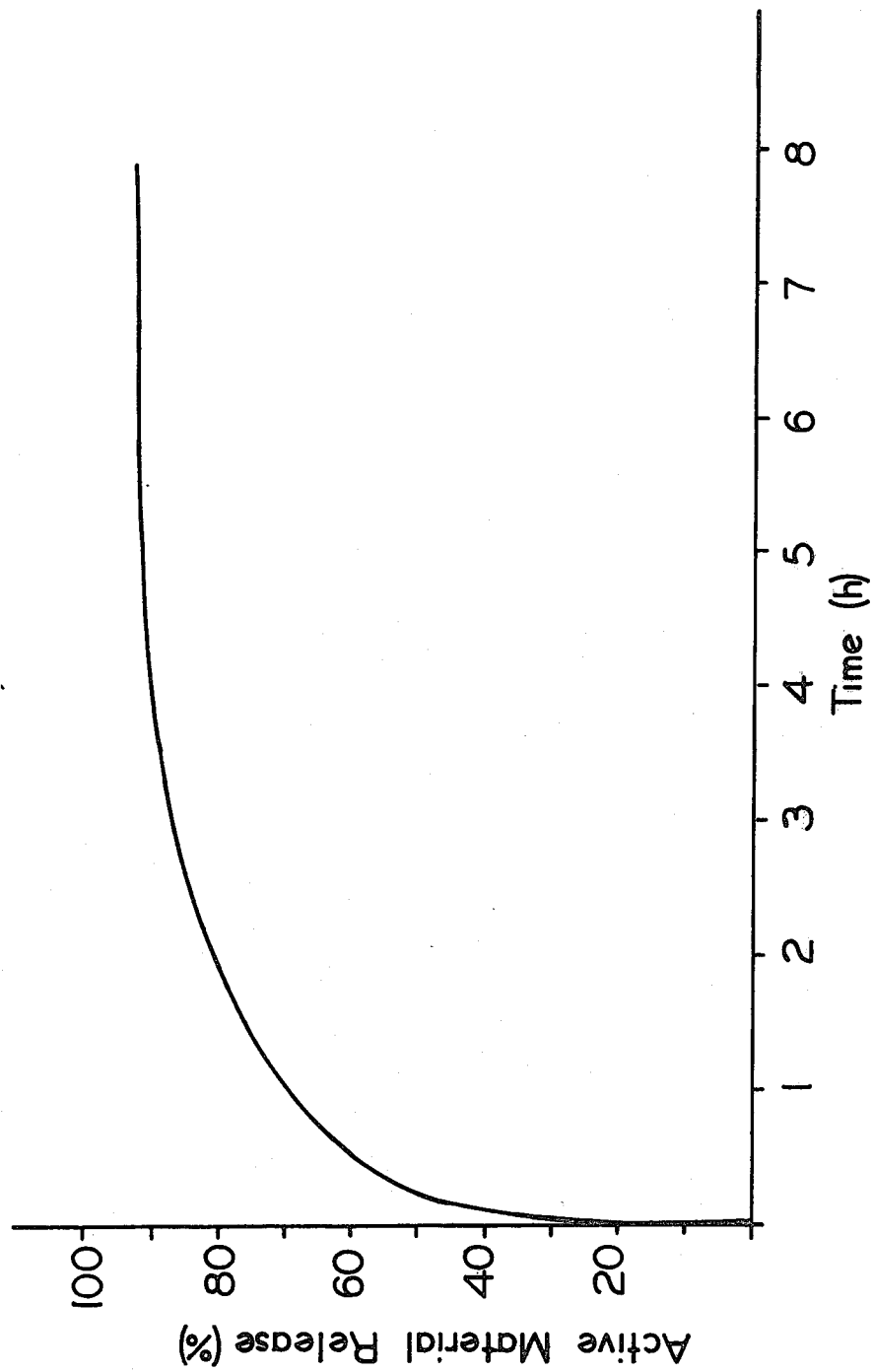

FIG. 11 illustrates the liberation of codeine at a pH of 2 (HCl). It is characterized by a high rate of liberation at the outset and a further release corresponding to that of the "matrix" type.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. A process for the incorporation of an active material into a silicon dioxide-containing carrier material, which comprises encapsulating the active material with liquid polyalkoxysiloxane, polyorgano-alkoxysiloxane or a mixture thereof by dissolving, suspending, emulsifying or dispersing the active material in the liquid siloxane to achieve a uniform distribution of the active material particles in the siloxane; and subsequently effecting hydrolytic polycondensation of the siloxane, whereby the active material is uniformly distributed in the composition produced.

2. The process of claim 1, wherein the alkoxy groups of polyalkoxysiloxane and the polyorganoalkoxysiloxane possess 1 to 4 C-atoms.

3. The process of claim 1, wherein the hydrolytic polycondensation is carried out by addition of gaseous water and gaseous $NH_3$.

4. The process of claim 1, wherein the hydrolytic polycondensation is carried out so that the resultant enveloping layer possesses a thickness of about 1 to 120 μm.

5. The process of claim 1, wherein the hydrolytic polycondensation is carried out so that the pore diameter of the resultant enveloping layer is about 20 to 400 Å.

6. The process of claim 1 which comprises dispersing the active material in liquid polyalkoxysiloxane, polyorganoalkoxysiloxane or a mixture thereof and subsequently hydrolytically polycondensing the siloxane.

7. The process of claim 1, wherein the encapsulating takes place in the presence of a solvent for the siloxane.

8. The process of claim 1, which comprises suspending the active material in liquid polyalkoxysiloxane, polyorganoalkoxysiloxane or a mixture thereof and dispersing the resultant suspension with stirring in water containing a polycondensation catalyst.

9. A composition comprising an active material and a silicon dioxide-containing carrier which is prepared by the process of claim 1.

10. A method of administering an active material with controlled release properties which comprises administering the active ingredient as a composition according to claim 9.

11. A process for incorporation of particles of an active material attached to a first carrier into a silicon dioxide-containing carrier material, which comprises encapsulating the particles of active material attached to the first carrier with liquid polyalkoxysiloxane, polyorgano-alkoxysiloxane or a mixture thereof by suspending or dispersing the particles of active material attached to the first carrier in the absence of water in the liquid siloxane or a solution thereof; when a solution is used, subsequently evaporating the solvent to achieve a uniform coating of the active material particles with the siloxane; and then hydrolytically polycondensing the siloxane whereby the particles of the active material attached to the first carrier are uniformly distributed in the composition produced.

12. The process of claim 11, wherein the carrier is porous, spheroidal silica gel.

* * * * *